United States Patent [19]

Kawamura et al.

[11] Patent Number: 5,302,699

[45] Date of Patent: Apr. 12, 1994

[54] ANTITUMORIGENIC PROTEIN, METHOD OF PREPARING IT AND ANTITUMORIGENIC COMPOSITION CONTAINING THE PROTEIN AS ACTIVE COMPONENT

[75] Inventors: Yukio Kawamura, Tsukuba; Akihiro Morita, Kasukabe; Makoto Tomatsu, Tsukuba; Masaru Ishikawa, Koshigaya, all of Japan

[73] Assignees: Director of National Food Research Institute, Ministry of Agriculture, Forestry and Fisheries, Tsukuba; Momoya Co., Ltd., Tokyo, both of Japan

[21] Appl. No.: 7,754

[22] Filed: Jan. 22, 1993

[30] Foreign Application Priority Data

Sep. 4, 1992 [JP] Japan .................. 4-260532

[51] Int. Cl.⁵ .................. A61K 35/80; C07K 3/22
[52] U.S. Cl. .................. 530/371; 530/370; 530/415; 530/416; 530/417
[58] Field of Search ............ 530/371, 370, 415, 416, 530/417

[56] References Cited

U.S. PATENT DOCUMENTS 4,207,312  6/1980  Fujii et al. .................. 424/80

FOREIGN PATENT DOCUMENTS 53-107407  9/1978  Japan .
5-70362    3/1993  Japan .

OTHER PUBLICATIONS

E. L. V. Harris et al., "Protein Purification Methods", IRL Press, 1989, pp. 9-10, 57-65.

Primary Examiner—Michael G. Wityshyn
Assistant Examiner—C. Sayala
Attorney, Agent, or Firm—Frishauf, Holtz, Goodman & Woodward

[57] ABSTRACT

Disclosed is an antitumorigenic protein derived from fruit bodies of matsutake mushrooms (*Tricholoma matsutake*). Also disclosed is a method of preparing the antitumorigenic protein comprising extracting fruit bodies of matsutake mushrooms with water followed by subjecting the resulting extract to purification composed of combination of the following three purifying steps in any desired order:

(1) a step of purifying the protein by molecular sieve chromatography in a gel permeation column;
(2) a step of bringing the extract in contact with an anion exchange resin so that the protein is adsorbed to the resin followed by eluting the protein from the column of the resin with an eluent; and
(3) a step of bringing the extract in contact with a hydrophobic chromatographic resin so that the protein is adsorbed to the resin followed by eluting the protein from the column of the resin with an eluent.

Further disclosed is an antitumorigenic composition to human and animal epithelial cancer, which contains the protein as an active component.

3 Claims, 6 Drawing Sheets

SDS-PAGE of Phenyl-superose

Native-PAGE

○ Balb/A31
● Balb/SV40

ANTITUMORIGENIC PROTEIN, METHOD OF PREPARING IT AND ANTITUMORIGENIC COMPOSITION CONTAINING THE PROTEIN AS ACTIVE COMPONENT

FIELD OF THE INVENTION

The present invention relates to a novel antitumorigenic protein, a method of preparing it and an antitumorigenic composition to human and animal epithelial cancer containing the protein as an active component.

BACKGROUND OF THE INVENTION

It is well known that some carcinostatic substances are in fruit bodies, mycelia and baggasse of mushrooms. However, it is said that the essential effect and mechanism of the substance are estimated to enhance the immunity and to be an adjuvant effect. The substance responsible for this action is not identified. Chemotherapy to cancer using various chemical substances has a problem that normal cells are also killed along with cancer cells to cause strong harmful side effects.

Some of the present inventors already completed an invention relating to an antitumorigenic protein of an aqueous extract from fruit bodies of matsutake mushrooms (*Tricholoma matsutake*) (Japanese Patent Application No. 3-258402). The present invention is to further develop the prior invention to specify the protein and establish a method of preparing it.

SUMMARY OF THE INVENTION

The present invention has been made in consideration of the problem so as to develop a method of uniformly purifying an antitumorigenic protein from fruit bodies of matsutake mushrooms using the selective cytotoxicity of acting only on cancer cells without having any influence on normal cells as an antitumorigenic index and to clarify the characteristics of the protein. Precisely, in accordance with the present invention, a novel antitumorigenic protein is prepared with an index of selective cytotoxicity only to mouse fetal fibroblasts transformed (carcinogenized) with SV40 virus and/or SV40DNA, which carcinogenize in mice in the same function and mechanism as a human papiloma virus (HPV) to cause squamous cell carcinomas such as typical human uterine cancer, without having any cytotoxicity to normal cells, and a tumoricidal composition containing the protein as an active component is provided.

Specifically, the present invention provides a novel antitumorigenic protein derived from fruit bodies of matsutake mushrooms (*Tricholoma matsutake*), having the following physicochemical properties.

(a) Molecular weight:

By SDS polyacrylamide electrophoresis, the molecular weight of the subunit is from 100,000 to 110,000.

By gel permeation chromatography, the molecular weight of the protein is from 200,000 to 210,000.

(b) Ultraviolet absorption spectrum:
As shown in FIG. 1.

(c) Color:
Pale yellowish brown to pale brown.

(d) Amino acid composition (molar ratio):

| Amino Acid | Molar Ratio |
| --- | --- |
| Aspartic Acid | 15.2 |
| Glutamic Acid | 10.5 |
| Serine | 7.3 |
| Glycine | 8.8 |
| Histidine | 2.0. |
| Arginine | 3.4 |
| Threonine | 9.6 |
| Alanine | 7.5 |
| Proline | 8.7. |
| Tyrosine | 2.5 |
| Valine | 7.3 |
| Methionine | 1.9 |
| Cysteine | Not determined |
| Isoleucine | 3.6 |
| Leucine | 6.1 |
| Phenylalanine | 2.8 |
| Lysine | 2.6 |

The present invention also provides a method of preparing the novel tumoricidal protein comprising extracting fruit bodies of matsutake mushrooms with water followed by subjecting the resulting extract to purification composed of combination of the following purifying steps in any desired order:

(1) a step of purifying the protein by molecular weight fractionation in a gel permeation column;

(2) a step of bringing the extract in contact with an anion exchange resin so that the protein is adsorbed to the resin followed by eluting the protein from the column of the resin with an eluent; and (3) a step of bringing the extract in contact with a hydrophobic chromatographic resin so that the protein is adsorbed to the resin followed by eluting the protein from the column of the resin with an eluent.

The present invention further provides an antitumorigenic composition to human and animal epithelial cancer, which contains the protein as an active component.

DETAILED EXPLANATION OF THE INVENTION

The antitumorigenic protein of the present invention is a novel substance having the above-mentioned physicochemical properties. It may be prepared by extracting fruit bodies of matsutake mushrooms with water followed by subjecting the resulting extract to purification composed of combination of the above-mentioned purifying steps in any desired order.

The protein has an antitumorigenic activity as mentioned hereinafter, and it is expected to be useful as an antitumorigenic agent, especially to human and animal epithelial cancer.

The present invention will be explained in more detail by way of the following examples, which, however, are not intended to restrict the scope of the present invention.

EXAMPLE 1

(1) Purification of antitumorigenic protein:

Frozen fruit bodies of matsutake mushrooms were thawed and ground with a homogenizer. Two times volume of water was added thereto and stirred for several minutes for extraction and then subjected to centrifugation (8,000 rpm, 30 minutes) to obtain a crude extract. Ammonium sulfate was dissolved in this to form a 90% saturated solution. This was subjected to centrifugation to obtain a precipitate.

The precipitate was subjected to dialysis for de-salting and then concentrated by freeze-drying. This was then subjected to gel permeation, using Sepharose CL-4B (manufactured by Pharmacia Co.) as a carrier. The active fractions were collected, then freeze-dried and fed into an anion exchange gel column for absorption. After washed, the protein was eluted out from the column by linear concentration gradient with NaCl.

Figure 2A:
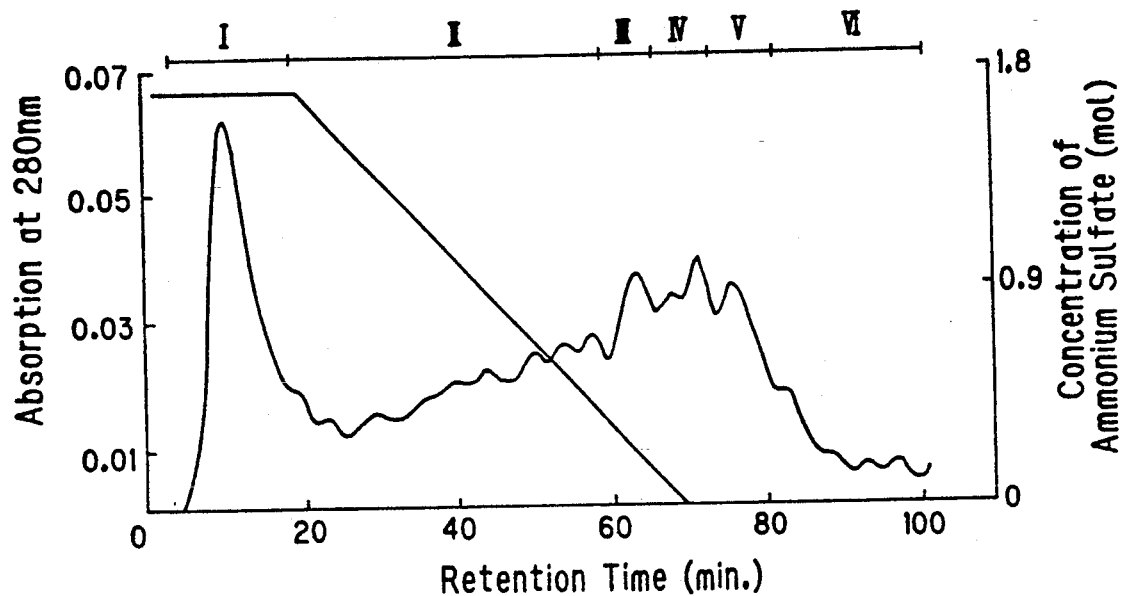
FIG. 2(A) shows an FPLC hydrophobic chromatographic pattern of a crude protein in Example 1 through a Phenyl-Superrose column, in which the protein was fractionated into fractions (I) to (VI)
Figure 2B:
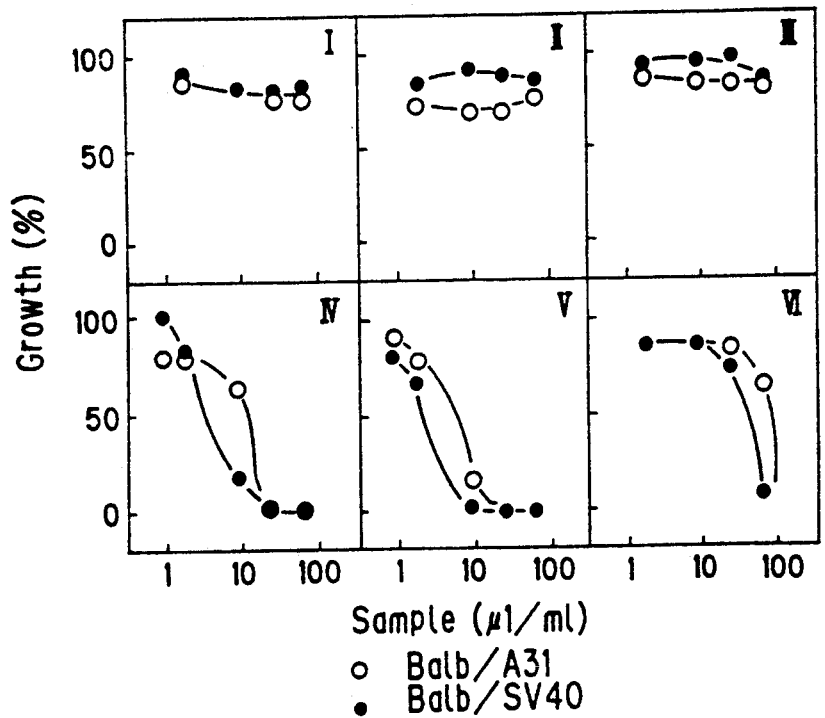
FIG. 2(B) shows a result of the measured tumoricidal activity of each fraction.
Figure 3:
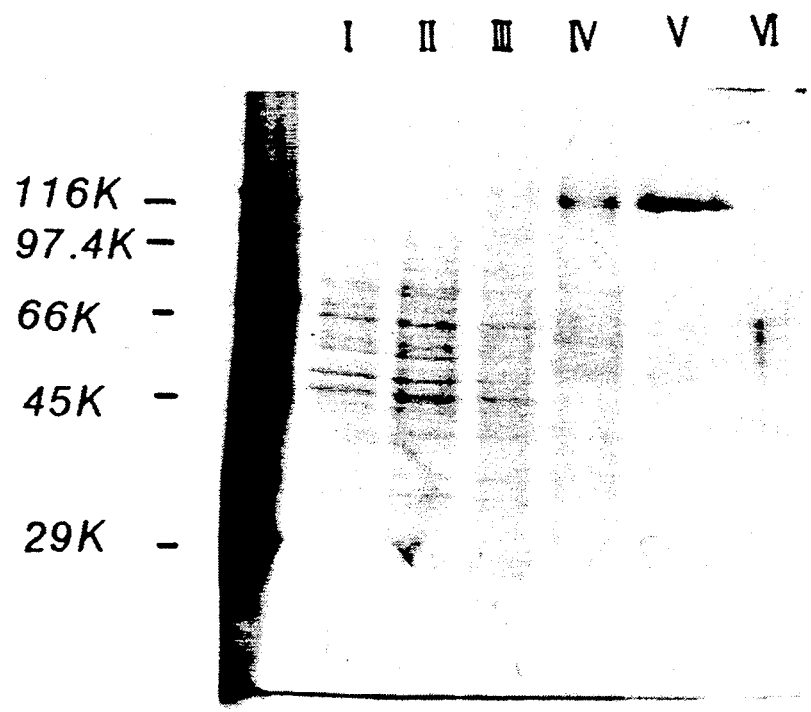
FIG. 3 shows an SDS-polyacrylamide gel electrophoresis pattern of the fractions (I to VI) resulting from the FPLC hydrophobic chromatography through the Phenyl-Superrose column.
Figure 4:
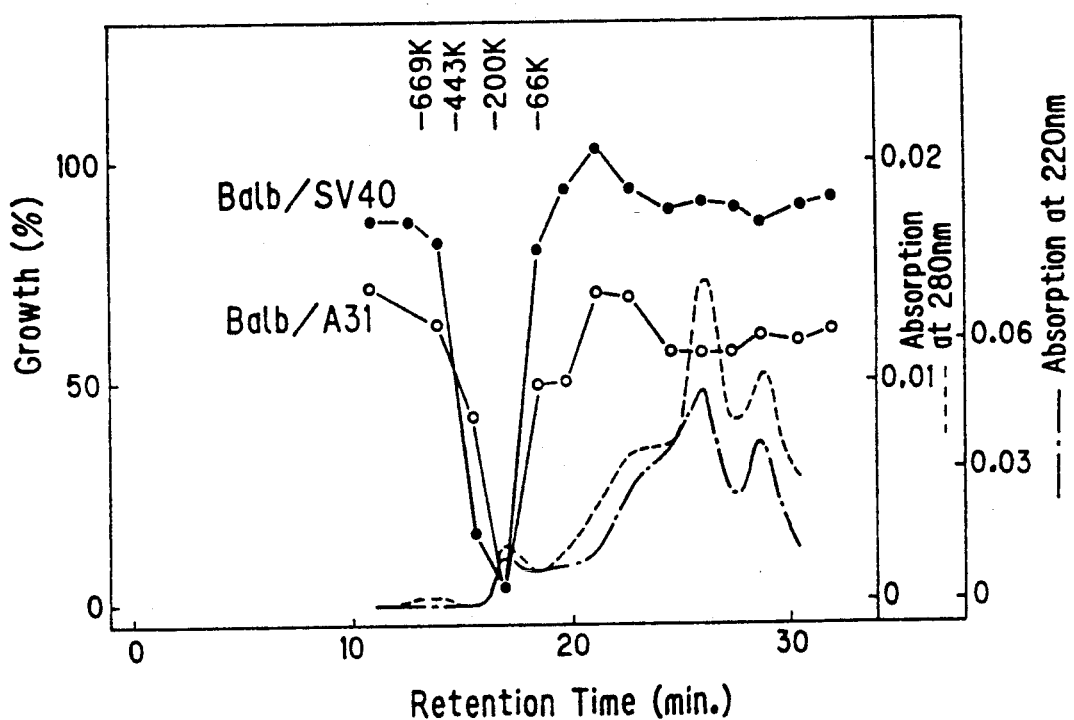
FIG. 4 shows an HPLC gel permeation pattern of the fraction (V) from the Phenyl-Superrose chromatography, through a TSK gel G3000 SWxL column.

Next, the protein was applied to a hydrophobic chromatography, using Phenyl-Superose (manufactured by Pharmacia Co.) for absorption. After washed, the protein was eluted out from the column by linear concentration gradient with ammonium sulfate. The protein was fractionated into six fractions of (I) to (VI), the activity of each of which was measured to reveal the fact that the fraction (V) had the strongest activity, as shown in FIG. 2(A) and FIG. 2(B). In FIG. 2(B), ○—○ shows normal cells (Balb/A31); and ●—● shows tumor cells (Balb/SV40). FIG. 3 shows a pattern of SDS-polyacrylamide gel electrophoresis of each fraction. The fraction (V) was shown to contain an antitumorigenic protein having a molecular weight of approximately from 100 to 110K. The fraction (V) was subjected to dialysis and then uniformly purified by HPLC gel permeation, using a TSK gel G3000SWxL column (refer to FIG. 4). An antitumorigenic protein was eluted in the position indicating a molecular weight of from 200 to 210K.

Figure 5A:
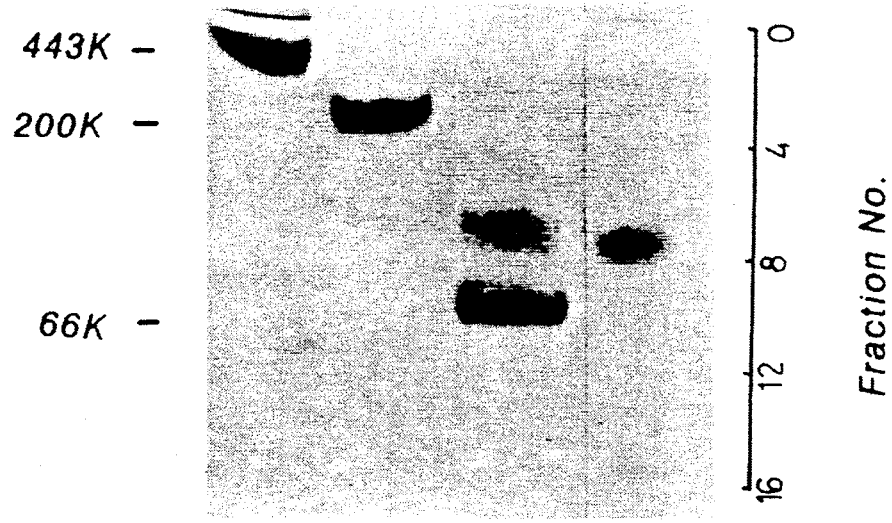
FIG. 5(A) shows a pattern of 6.5% Native-PAGE of a purified protein.
Figure 5B:
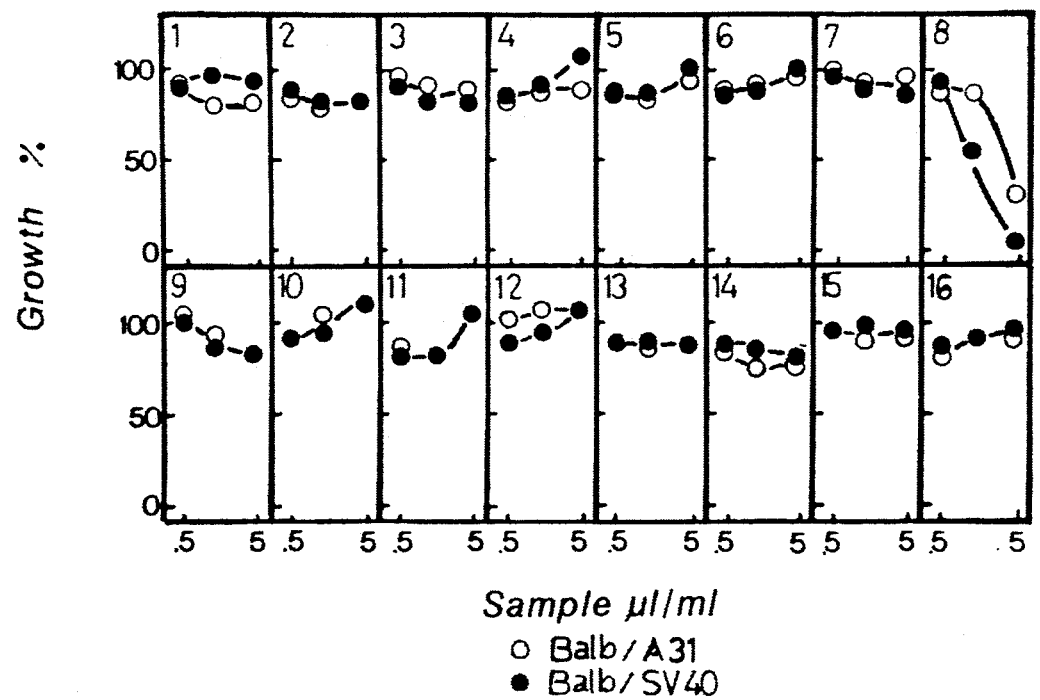
FIG. 5(B) shows an antitumorigenic activity of the protein from the sample gel of lane S.

(2) Characteristics of protein:

Purity:

After polyacrylamide electrophoresis, the gel was sliced into 16 pieces, the protein was electrically extracted from each sliced gel and subjected to dialysis, and the activity of the resulting proteins was measured. In FIG. 5(A), lane I indicates apoferritin, lane II indicates $\beta$-amylase, lane III indicates BSA, and lane S indicates a sample. The sample gel of lane S was equally divided into 16 parts, a protein was electrically extracted from each part and the antitumorigenic activity of the extracted protein was measured. FIG. 5(B) shows the result. As is obvious from FIG. 5(B), only the part No. 8 was admitted to have the activity, and it corresponded to the band in the position of the lane S. Accordingly, the antitumorigenic (tumoricidal) protein was identified to move at the position of the relative mobility of about 0.5 (refer to FIG. 5(A) and FIG. 5(B)).

Figure 6:
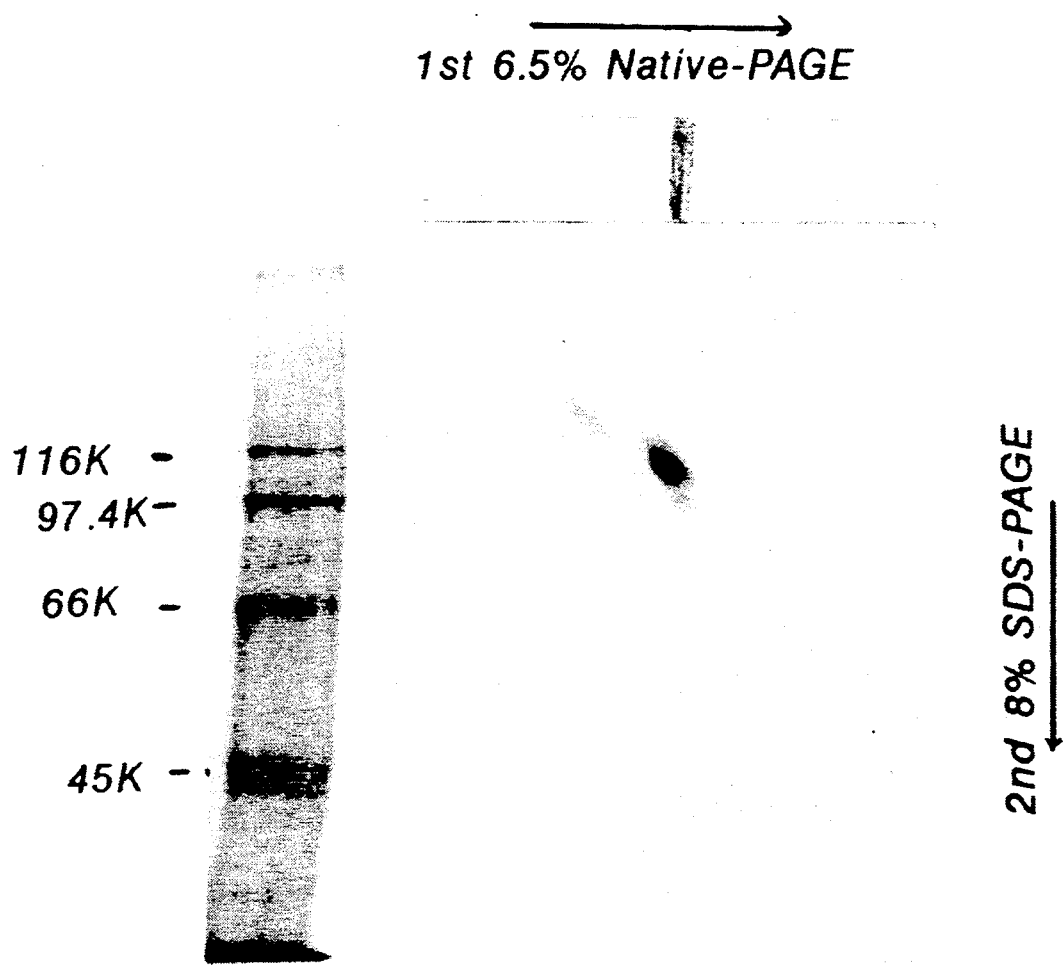
FIG. 6 shows a two-dimensional electrophoresis pattern composed of 6.5% Native-PAGE electrophoresis of the first dimension followed by 8% SDS-PAGE electrophoresis of the second dimension.

FIG. 6 shows the result of two-dimensional electrophoresis comprising polyacrylamide electrophoresis (6.5% Native-PAGE) of the first dimension followed by SDS electrophoresis (8% SDS-PAGE) of the second dimension. In FIG. 6, lane St indicates standard proteins for calculating the molecular weight.

At the position of the relative mobility of 0.5 in the first dimension, appeared one spot, which was presumed to have a subunit molecular weight of from 100,000 to 110,000 from the standard protein for estimation or calibration of the molecular weight in the second dimension. No spot was observed in any other position, indicating that the protein was uniformly purified. Along with the result of the above-mentioned HPLC gel permeation chromatography, the protein was estimated to be homodimer with a native molecular weight of from 200,000 to 210,000 and comprised two subunits each having a molecular weight of from 100,000 to 110,000.

Amino Acid Composition:

The present antitumorigenic protein purified in a homogeneous state by the manner mentioned above was subjected to amino acid composition analysis, and the result is as shown in claim 1.

(3) Measurement of Antitumorigenic Activity and Antitumorigenic Spectrum:

The antitumorigenic activity of the protein was determined by measuring the number of viable cell with MTT method. The MTT method is an in vitro measuring method for viability, which is evaluated to have high relation to in vivo measurement. The antitumorigenic activity of the protein thus measured was represented as percentage (%) to the number of the control cells. As a result, $LD_{50}$ (50% Lethal concentration) of the purified protein to mouse fibroblasts was about 7 ng/ml for transformed cells and about 30 ng/ml for normal cells. The puvified antitumorigenic protein was effective not only to mouse cells but also to human cells. $LD_{50}$ of the protein was about 14 ng/ml to human uterine cancer -derived Hela cells, about 8 ng/ml to the sub-strain Hela S3 cells, and about 4 ng/ml to W138VA13 subline 2RA which formed by transforming human fetal lung cells with SV40.

As mentioned above, the protein was identified to have a strong lethal effect not only to mouse cells but also to human cancer cells.

The present invention, provided a novel antitumorigenic protein, a method of producing it and an antitumorigenic composition containing the protein as an active component. The antitumorigenic protein has expressed an antitumorigenic activity to only cancer cells with little influence on normal cells, and therefore it is useful as an antitumorigenic agent, especially to human and animal epithelial cancer, cells.

While the invention has been described in detail and with reference to specific embodiments thereof, it will be apparent to one skilled in the art that various changes and modifications can be made therein without departing from the spirit and scope thereof.

Figure 1:
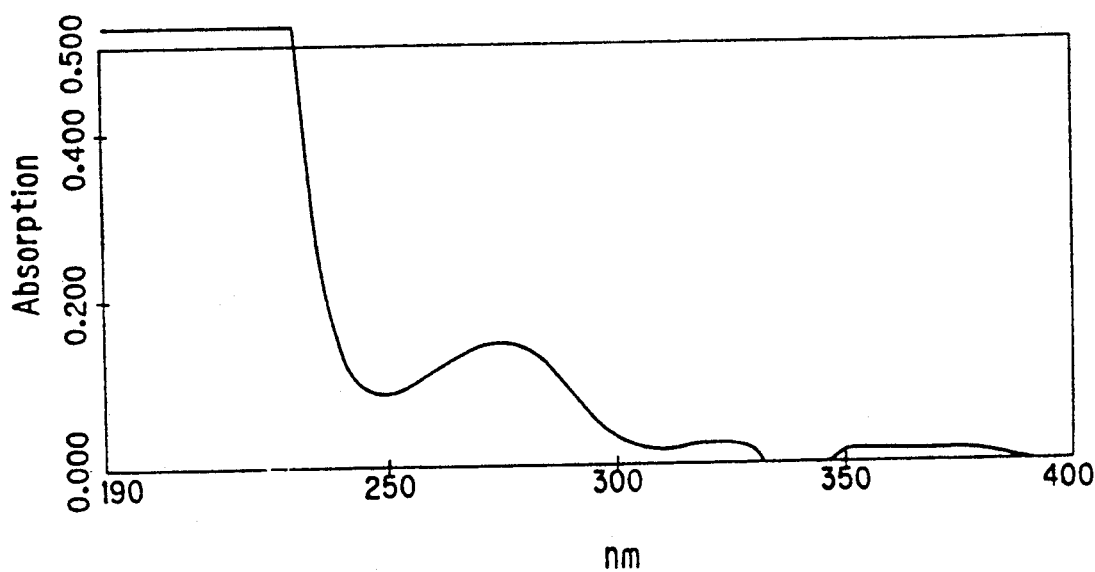
FIG. 1 shows an ultraviolet absorption spectrum of the antitumorigenic protein of the present invention.

What is claimed is:

1. A substantially pure antitumorigenic protein derived from fruit bodies of *Tricholoma matsutake* mushrooms, having the following physicochemical properties:

(a) molecular weight:

by SDS polyacrylamide electrophoresis, a molecular weight of the subunit is from 100,000 to 110,000;

by gel permeation chromatography, the molecular weight of the protein is from 200,000 to 210,000;

(b) ultraviolet absorption spectrum:
as shown in FIG. 1;

(c) color:
pale yellowish brown to pale brown;

(d) amino acid constitution (molar ratio):

| Amino Acid | Molar Ratio |
| --- | --- |
| Aspartic Acid | 15.2 |
| Glutamic Acid | 10.5 |
| Serine | 7.3 |
| Glycine | 8.8 |
| Histidine | 2.0 |
| Arginine | 3.4 |
| Threonine | 9.6 |
| Alanine | 7.5 |
| Proline | 8.7 |
| Tyrosine | 2.5 |
| Valine | 7.3 |
| Methionine | 1.9 |
| Isoleucine | 3.6 |
| Leucine | 6.1 |
| Phenylalanine | 2.8 |
| Lysine | 2.6. |

2. A method of preparing the substantially pure antitumorigenic protein as claimed in claim 1, which comprises extracting fruit bodies of *Tricholoma matsutake* mushrooms with water followed by subjecting the resulting extract to purification comprising the following three purifying steps in any desired order:

(1) a step of purifying the extract by molecular sieve chromatography in a gel permeation column;

(2) a step of bringing the extract in contact with an anion exchange resin so that the protein is adsorbed to the resin followed by eluting the protein from the column of the resin with an eluent; and (3) a step of bringing the extract in contact with a hydrophobic resin so that the protein is adsorbed to the resin followed by eluting the protein from the column of the resin with an eluent;

and recovering said substantially pure protein.

3. An antitumorigenic composition to human and animal epithelial cancer, which contains a protein as claimed in claim 1 as an active component and an excipient.

* * * * *